United States Patent [19]

Fridinger et al.

[11] 4,116,676

[45] Sep. 26, 1978

[54] 4-METHYLTHIO-2-TRIFLUOROME-THYLMETHANE-SULFONANILIDE AND DERIVATIVES THEREOF

[75] Inventors: Tomas L. Fridinger, Woodbury; George G. I. Moore, Birchwood; Larry R. Lappi, Stillwater, all of Minn.

[73] Assignee: Minnesota Mining and Manufacturing Company, St. Paul, Minn.

[21] Appl. No.: 739,133

[22] Filed: Nov. 5, 1976

Related U.S. Application Data

[62] Division of Ser. No. 523,673, Nov. 14, 1974, Pat. No. 3,996,277.

[51] Int. Cl.$^2$ .............................................. A01N 9/16
[52] U.S. Cl. ................... 71/103; 260/609 F; 260/576; 260/556 F

[58] Field of Search .......................................... 71/103

[56] References Cited

U.S. PATENT DOCUMENTS

| | | |
|---|---|---|
| 3,799,968 | 3/1974 | Harrington et al. ................ 71/103 |
| 3,856,859 | 12/1974 | Moore et al. .................... 260/556 A |
| 3,920,444 | 11/1975 | Harrington et al. ................ 71/103 |
| 3,948,987 | 4/1976 | Fridinger ...................... 260/556 F |

*Primary Examiner*—Catherine L. Mills
*Attorney, Agent, or Firm*—Cruzan Alexander; Donald M. Sell; Donald C. Gipple

[57] ABSTRACT

2-(Trifluoromethyl)methanesulfonanilides substituted in the para position by methylthio, methylsulfinyl or methylsulfonyl groups and horticulturally acceptable salts thereof and composition containing these compounds are useful herbicides.

7 Claims, No Drawings

4-METHYLTHIO-2-TRIFLUOROMETHYLME-THANE-SULFONANILIDE AND DERIVATIVES THEREOF

This application is a division of our copending application Ser. No. 523,673, filed Nov. 14, 1974, now U.S. Pat. No. 3,996,277.

This invention relates to 2-(trifluoromethyl)methanesulfonanilides substitued in the para position by methylthio, methylsulfinyl or methylsulfonyl groups and horticulturally acceptable salts thereof and composition containing these compounds. The compounds of the invention are active herbicidal agents and, in many cases, are also active plant growth modifying agents. Specifically, the invention includes the compounds 4-methylthio-2-trifluoromethylmethanesulfonanilide, 4-methylsulfinyl-2-trifluoromethylmethanesulfonanilide and 4-methylsulfonyl-2-trifluoromethylmethanesulfonanilide and agriculturally acceptable salts thereof. The invention also relates to herbicidal formulations containing said compounds and to the use of the compounds to regulate and control the growth of higher plants. Methods for preparing the compounds and intermediates in their preparation are also included.

BACKGROUND OF THE INVENTION

Several classes of haloalkylsulfonamido-substituted aromatic compounds have been known heretofore, as have certain uses for these compounds. Thus, U.S. Pat. No. 3,639,474 discloses trifluoromethanesulfonanilides, including such compounds with trifluoromethyl, methylthio, methylsulfinyl and methylsulfonyl substituents, to be useful as herbicides. French Pat. No. 1,188,591 includes disclosures of two classes of compounds, i.e. haloalkylsulfonanilides and haloalkylsulfonamidodiphenyl compounds in which the rings are bonded directly or are linked by various groups including sulfonyl, sulfinyl and thio groups. The areas of utility disclosed by the French patent include activity against textile material parasites as well as antibacterial and anti-mildew activity. Herbicidal activity is not disclosed in that patent however. British Patent 971,219 discloses alkanesulfonanilides containing both chlorine and nitro ring substituents to have herbicidal activity.

The present invention provides a limited class of novel compounds which contain a non-fluorinated methanesulfonamido group and which have a unique and particularly valuable spectrum of activity. They are especially effective in controlling established rhizomatous Johnson Grass (*Sorghum halepense* (L. Pers.)). This is of significance since while seedling Johnson Grass is susceptible to several commercial herbicides, rhizomatous Johnson Grass is not controlled effectively at application rates of such materials that are tolerated by crops. It is unexpected to find such effective control of established rhizomatous Johnson Grass in the compounds of the invention. The compounds of the invention have also been found to be particularly effective in controlling nutsedge (for example *Cyperus esculentus*) species.

DETAILED DESCRIPTION OF THE INVENTION

This invention relates to compounds of the formula

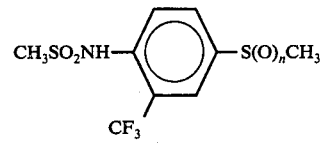

wherein "n" is zero, one or two and agriculturally acceptable salts thereof.

The invention also relates to compositions for killing and modifying the growth of higher plants consisting essentially of a compound of the invention dispersed in an extending medium.

The invention also relates to the use of the compounds of the invention to modify the growth of higher plants, and to kill higher plants.

This invention also relates to processes for the preparation of the compounds of the invention.

The acid-form compounds of the invention are acidic, i.e. the amido hydrogen is acidic. Consequently, they form salts, i.e. compounds of the above formula wherein H is replaced by an agriculturally acceptable cation. These are generally metal, ammonium, and organic amine salts and can be prepared by treating the acid form compound with a stoichiometrically equivalent amount of an appropriate base under mild conditions. Among the metal salts of the invention are alkali metal (e.g. lithium, sodium and potassium), alkaline earth metal (e.g. barium, calcium and magnesium) and heavy metal (e.g. zinc and iron) salts as well as other metal salts such as aluminum. Appropriate bases for use in preparing the metal salts include metal oxides, hydroxides, carbonates, bicarbonates and alkoxides. Some salts are also prepared by cation exchange reaction (by reacting a salt of the invention with an organic or inorganic salt in a cation exchange reaction). The organic amine salts include the salts of aliphatic (e.g. alkyl), aromatic and heterocyclic amines, as well as those having a mixture of these types of structures. The amines useful in preparing the salts of the invention can be primary, seondary or tertiary and preferably contain not more than 20 carbon atoms. Such amines include, for example, morpholine, methyl cyclohexylamine, glucosamine, amines derived from fatty acids, etc. The amine and ammonium salts can be prepared by reacting the acid form with the appropriate organic base or ammonium hydroxide. Any of the salts of the types set out above are agriculturally acceptable, the one chosen depending upon the particular use and upon the economics of the situation. Of particular utility are the alkali metal, alkaline earth, ammonium and amine salts.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetone, etc. The resulting solution is then treated to remove the solvent, for example, by evaporation under reduced pressure. Since many of the salts are water soluble, they are often used in the form of aqueous solutions.

The compounds of the invention can be prepared according to the reaction sequences outlined below.

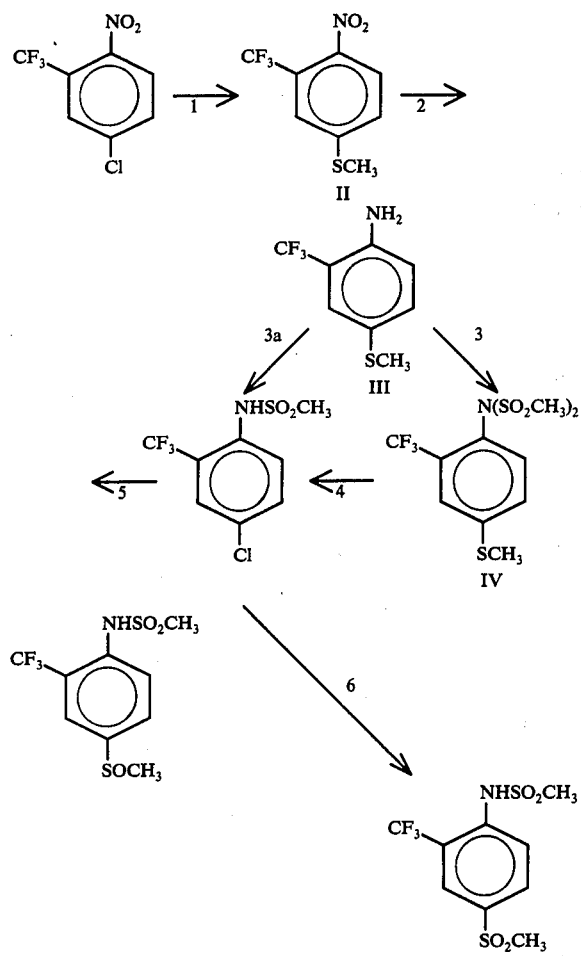

The reaction of step 1 is carried out by heating 5-chloro-2-nitrobenzotrifluoride and a slight excess of methanethiol in a suitable inert solvent in the presence of the appropriate amount of base. The inert solvent is one in which the reactants are soluble such as a lower alkanol, e.g. ethanol. The base is a strong organic or inorganic base. Suitable organic bases are tertiary amines such as N,N-dimethylaniline, triethylamine, pyridine, alkoxides such as sodium ethoxide and the like. Suitable inorganic bases are alkali metal hydroxides, such as sodium and potassium hydroxides, calcium hydride and the like. The product is isolated by conventional methods.

The reaction of step 2 is a reduction of the nitro-group of the novel intermediate 2-nitro-5-methylthiobenzotrifluoride (II). Chemical or catalytic methods well known to the art are successful. Raney nickel is one suitable catalyst for the reduction. The product is isolated by conventional methods.

The reaction of step 3 is the bis(methylsulfonylation) of the novel intermediate 4-methythio-2-trifluoromethylaniline (III) with two or more moles of methanesulfonylchloride in the presence of excess base. The product obtained is the novel intermediate (IV). Alternatively step 3a is the mono(methylsulfonylation) of III with one equivalent of methanesulfonylchloride in the presence of one equivalent of base in an inert solvent. Suitable bases for the reactions of steps 3 and 3a are organic or inorganic bases such as pyridine, triethylamine, N,N-dimethylaniline and substituted pyridines, and the like.

Step 4 is partial hydrolysis of the novel intermediate (IV). This is a high yield base hydrolysis reaction using a strong base such as potassium hydroxide in methanol.

Steps 5 and 6 are both carried out using conventional oxidation methods such as hydrogen peroxide in acetic acid, sodium metaperiodate and the like. Step 5 requires equimolar amounts of peroxide and reactant, while step 6 utilizes two moles (or slight excess) of oxidizing agent per mole of reactant.

The herbicidal activity of the compounds of the invention has been determined using screening tests against greenhouse plantings. Both pre- and post-emergence activity are determined in a direct screen against selected weed species. The following weeds are examples of weeds which are used for these tests.

Grasses

Giant foxtail (*Setaria faberii*)
Barnyard grass (*Echinochloa crusgalli*)
Crabgrass (*Digitaria ischaemum*)
Quackgrass (*Agopyron repens*)
Yellow Nutsedge (*Cyperus esculentus*)

Broadleaves

Pigweed (*Amaranthus retroflexus*)
Purslane (*Portulaca oleracea*)
Wild Mustard (*Brassica kaber*)
Wild Morning Glory (*Convolvulus arvensis*)

The test chemicals are dissolved in a small amount of acetone or other suitable solvent and then diluted with water to give a concentration of 2000 ppm. From this concentration aliquots are diluted to give a final concentration of 500 ppm. Eighty ml. of this solution are added to a 6-inch pot containing the weed seeds to give a concentration equivalent to 20 lb./acre. Use of 20 ml. of said solution gives a concentration equal to 5 lb./acre. All subsequent waterings are made from the bottom. Two pots are used per treatment. Data are taken two to three weeks after treatment and recorded as percent pre-emergence kill for each species compared to the untreated controls.

To assess post-emergence activity, the same weed mixtures are allowed to grow from two to three weeks until the grasses are approximately 1 to 3 inches and the broadleaves 1 to 1½ inches tall. They are sprayed for approximately 10 seconds or until good wetting of the leaf surfaces occurs with a 2000 ppm solution as described above.

Data are taken two to three weeks after treatment and recorded as percent kill for each species compared to the untreated controls.

The compounds of this invention are broadly active as herbicides. The mechanism(s) by which this herbicidal activity is effected is not presently known. However, many of the compounds of this invention also show various types of plant growth modifying activity. Plant growth modification as defined herein consists of all deviations from natural development, for example, defoliation, stimulation, stunting, retardation, dessication, tillering, dwarfing, regulation and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants.

As noted previously, the compounds of the invention have been found to be particularly effective in controlling established rhizomatous Johnson Grass (*Sorghum halepense* (L. Pers.)) and nutsedge (for example *Cyperus esculentus*) species. The control of rhizomatous Johnson Grass especially important since it is not controlled effectively at an application rate that is tolerant to crops by commercially available herbicides (although seedling Johnson Grass is susceptible to several commercial herbicides).

For application to plants, the compounds can be finely divided and suspended in any of the usual aqueous media. In addition, spreading agents, wetting agents, sticking agents or other adjuvants can be added as desired. Dry powders, as such or diluted with inert materials such as diatomaceous earth, can likewise be used as dusts for this purpose. The preparations are coated on the plants or the ground is covered when pre-emergence control is desired. Application is made with the usual sprayers, dust guns and the like. Application rates are at 0.5 to 20 lbs./acre in general, but may be increased or reduced according to individual circumstances of use.

Since certain compounds of the invention are particularly active against Johnson grass, it is particularly advantageous to combine them with other known herbicides to broaden or maximize the weed spectrum controlled by herbicidal compositions of this invention or to better control a weed not well controlled by specific compounds of the invention. Among these other known herbicides are phenoxy herbicides, e.g. 2,4-D; 2,4,5-T, Silvex and the like, carbamate herbicides, thiocarbamate and dithiocarbamate herbicides, substituted urea herbicides, e.g. diuron, monuron, and the like, triazine herbicides, e.g. simazine and atrazine, chloroacetamide and chlorinated aliphatic acid herbicides, chlorinated benzoic and phenylacetic acid herbicides such as chloramben and other herbicides such as trifluralin, paraquat, nitralin and the like. Furthermore, herbicidal compositions containing compounds of the invention may contain, in addition, nematicides, fungicides, insecticides, fertilizers, trace metals, soil conditioners, other plant growth regulators and the like. Such combinations are clearly envisioned in this invention.

The following examples are given for the purpose of further illustrating the procedures of the present invention, but are not intended, in any way, to be limiting on the scope of the invention.

EXAMPLE 1

2-Nitro-5-methylthiobenzotrifluoride

The sodium salt of methanethiol is formed by stirring a solution of methanethiol (100 g, 2.0 mole plus a slight excess), sodium hydroxide (80 g, 2.0 mole) and ethanol (2 l.) under nitrogen at 0°–5° C. for one hour. To this solution is rapidly added 5-chloro-2-nitrobenzotrifluoride (451.2 g, 2.0 mole). The solution is allowed to warm to room temperature overnight and then refluxed four hours, cooled, filtered and the solvent evaporated off under reduced pressure. The resulting oil is poured into cold water (1 l.), extracted with methylene chloride, dried over magnesium sulfate and the solvent evaporated under reduced pressure to afford a yellow solid. Recrystallization from hexane affords a product having a melting point of 47°–50° C.

Analysis: %C; %H; %N; Calculated for $C_8H_6F_3NO_2S$: 40.5; 2.5; 5.9; Found: 40.4; 2.5; 5.6.

EXAMPLE 2

4-Methylthio-2-trifluoromethylaniline

2-Nitro-5-methylthiobenzotrifluoride (190 g, 0.85 mole) in ethanol (1 l.) is reduced over Raney nickel at about 45 psi of hydrogen gas. After hydrogen uptake is complete the catalyst is deactivated with elemental sulfur, the mixture is filtered, and the filtrate evaporated under reduced pressure to afford the desired product as an oil. IR 2.9μ (strong NH band).

EXAMPLE 3

N-Methylsulfonyl-4-methylthio-2-trifluoromethylmethanesulfonanilide

Methanesulfonyl chloride (21.8 g, 0.19 mole) is added dropwise to a cold (0°–10° C.) stirred solution of 4-methylthio-2-trifluoromethylaniline prepared according to Example 2 (15.8 g., 0.076 mole) in pyridine (48 g, 0.61 mole). The solution is stirred at room temperature overnight, poured into ice water (80 ml) and concentrated hydrochloric acid (20 ml) and the resulting solid dissolved in methylene chloride, dried over magnesium sulfate, and the solvent evaporated under reduced pressure. The product is recrystallized from a hexane-methylene chloride mixture to give a white solid, m.p. 147°–154° C.

Analysis: %C; %H; %N; Calculated for $C_{10}H_{12}F_3NO_4S_3$: 33.1; 3.3; 3.9; Found: 32.9; 3.3; 3.8.

EXAMPLE 4

4-Methylthio-2-trifluoromethylmethanesulfonanilide

A mixture of N-methylsulfonyl-4-methylthio-2-trifluoromethylmethanesulfonanilide (545 g, 1.5 mole), 85% potassium hydroxide (297 g., 4.5 mole) and methanol (2 l.) is stirred overnight at room temperature. The solvent is evaporated under reduced pressure and the resulting solid dissolved in hot water. The solution is filtered and the filtrate acidified with dilute hydrochloric acid. Product is isolated by extraction with methylene chloride, drying over magnesium sulfate followed by evaporation of the solvent under reduced pressure to yield a beige solid, m.p. 82°–85° C.

Analysis: %C; %H; %N; Calculated for $C_9H_{10}F_3NO_2S_2$: 37.9; 3.5; 4.9; Found: 38.0; 3.7; 4.9.

EXAMPLE 5

4-Methylsulfinyl-2-trifluoromethylmethanesulfonanilide

To a cold (0°–5° C.) stirred mixture of 4-methylthio-2-trifluoromethylmethanesulfonanilide (118.5 g, 0.42 mole) in glacial acetic acid (470 ml) is added 30% hydrogen peroxide (47.3 g, 0.42 mole). The solution is stirred at 0°–5° C. for six hours, allowed to warm to room temperature overnight, diluted with water (1000 ml) and extracted with methylene chloride. The extract is further washed with water, dried over magnesium sulfate and the product precipitated with hexane as a white solid, m.p. 123°–125° C.

Analysis: %C; %H; %N; Calculated for $C_9H_{10}F_3NO_3S_2$: 35.9; 3.3; 4.7; Found: 35.9; 3.4; 4.6.

EXAMPLE 6

4-Methylsulfonyl-2-trifluoromethylmethanesulfonanilide

To a warm (60° C.) stirred solution of 4-methylthio-2-trifluoromethylmethanesulfonanilide (105.6 g, 0.37 mole) in glacial acetic acid (350 ml), 30% hydrogen peroxide (170 g, 1.49 mole) is added dropwise at such a rate that refluxing is maintained with little or no external heating. The solution is heated at reflux for an additional 2 hours, water (250 ml) is added, and the mixture is cooled. The precipitate is collected by filtration, washed with water, and dried to give a white solid, m.p. 177°–181° C.

Analysis: %C; %H; %N; Calculated for $C_9H_{10}F_3NO_4S_2$: 34.1; 3.2; 4.4; Found: 34.1; 3.2; 4.4.

What is claimed is:

1. A method for supressing or inhibiting the growth of higher plants which comprises contacting said plants with an effective amount of a compound of the formula

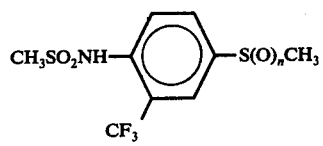

wherein n is zero, one or two and agriculturally acceptable salts thereof.

2. A composition for supressing or inhibiting the growth of higher plants which consists essentially of a compound according to claim 1 dispersed in an extending medium.

3. A method according to claim 1 for controlling the growth of rhiizomatous Johnsongrass which comprises contacting the same with an effective amount of a compound of the formula

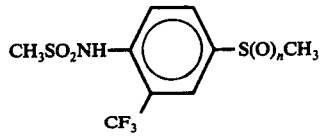

wherein n is zero, one or two or an agriculturally acceptable salt thereof.

4. A method according to claim 3 wherein the compound is 4-methylthio-2-trifluoromethylmethanesulfonanilide or an agriculturally acceptable salt thereof.

5. A method according to claim 3 wherein the compound is 4-methylsulfinyl-2-trifluoromethylmethanesulfonanilide or an agriculturally acceptable salt thereof.

6. A method according to claim 3 wherein the compound is 4-methylsulfonyl-2-trifluoromethylmethanesulfonanilide or an agriculturally acceptable salt thereof.

7. A composition according to claim 2 for controlling the growth of rhizomatous Johnsongrass which consists essentially of a compound of the formula

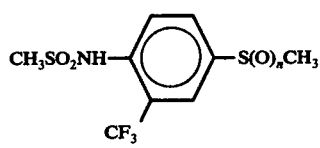

wherein n is zero, one or two or an agriculturally acceptable salt thereof dispersed in an extending medium.

* * * * *

UNITED STATES PATENT AND TRADEMARK OFFICE
CERTIFICATE OF CORRECTION

PATENT NO. : 4,116,676
DATED : September 26, 1978
INVENTOR(S) : Tomas L. Fridinger, George G. I. Moore and Larry R. Lappi It is certified that error appears in the above-identified patent and that said Letters Patent are hereby corrected as shown below:

The reaction sequence which is shown at the top of column 3 as the following:

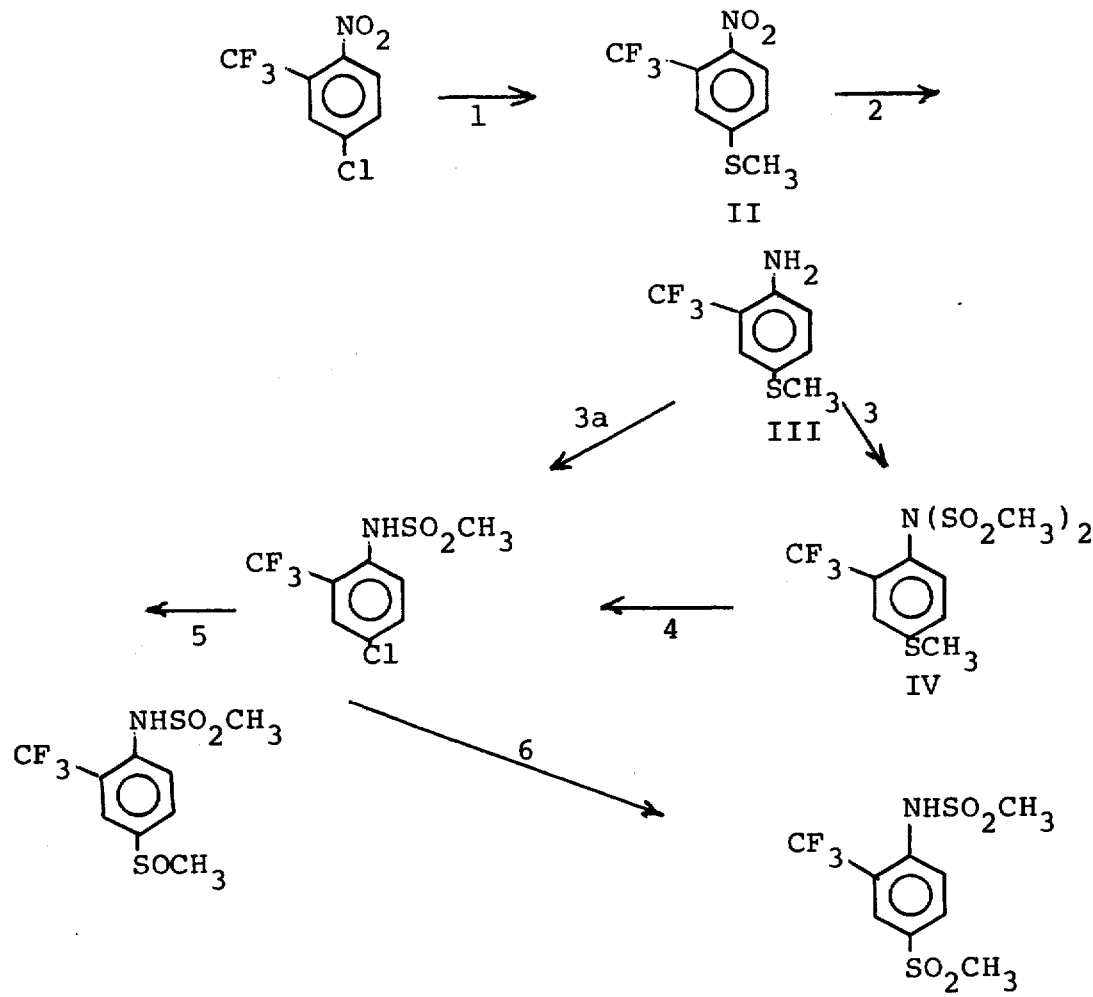

UNITED STATES PATENT OFFICE
CERTIFICATE OF CORRECTION

Patent No. 4,116,676        Dated September 26, 1978

Inventor(s) Tomas L. Fridinger et al.

It is certified that error appears in the above-identified patent and that said Letters Patent are hereby corrected as shown below:

should be shown as follows:

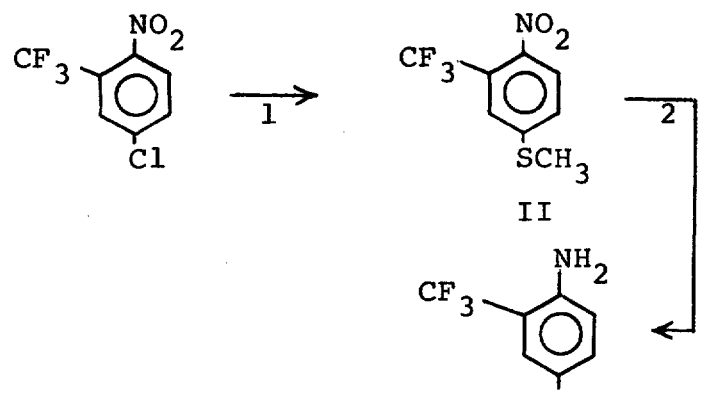

UNITED STATES PATENT OFFICE
CERTIFICATE OF CORRECTION

Patent No. 4,116,676　　　　　　　　　Dated September 26, 1978

Inventor(s) Tomas L. Fridinger et al.

It is certified that error appears in the above-identified patent and that said Letters Patent are hereby corrected as shown below:

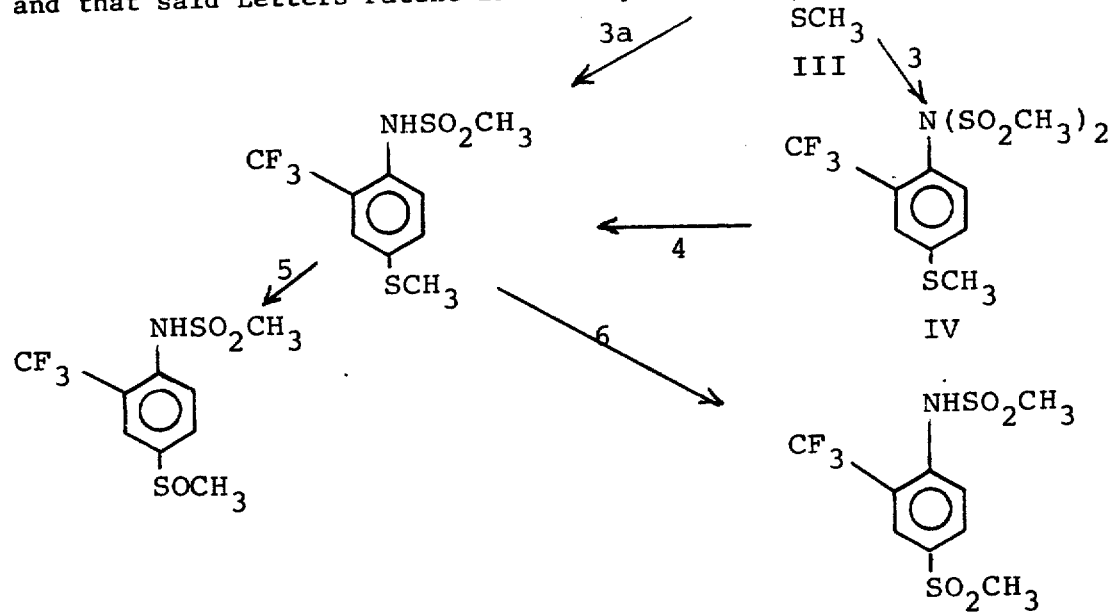

Signed and Sealed this

Thirtieth Day of January 1979

[SEAL]

Attest:

RUTH C. MASON
Attesting Officer

DONALD W. BANNER
Commissioner of Patents and Trademarks